(12) United States Patent
Gmeiner

(10) Patent No.: US 9,284,559 B2
(45) Date of Patent: Mar. 15, 2016

(54) MULTIVALENT APTAMER COMPLEXES

(75) Inventor: William H. Gmeiner, Yadkinville, NC (US)

(73) Assignee: Wake Forest University Health Sciences, Winston-Salem, NC (US)

( * ) Notice: Subject to any disclaimer, the term of this patent is extended or adjusted under 35 U.S.C. 154(b) by 284 days.

(21) Appl. No.: 12/759,216

(22) Filed: Apr. 13, 2010

(65) Prior Publication Data

US 2010/0261781 A1 Oct. 14, 2010

Related U.S. Application Data

(60) Provisional application No. 61/169,058, filed on Apr. 14, 2009.

(51) Int. Cl.
*C12N 15/11* (2006.01)
*C12N 15/115* (2010.01)

(52) U.S. Cl.
CPC .......... *C12N 15/115* (2013.01); *C12N 2310/16* (2013.01); *C12N 2310/3519* (2013.01)

(58) Field of Classification Search
CPC combination set(s) only.
See application file for complete search history.

(56) References Cited

U.S. PATENT DOCUMENTS

| | | | |
|---|---|---|---|
| 5,457,187 A | 10/1995 | Gmeiner et al. | |
| 5,614,505 A | 3/1997 | Gmeiner et al. | |
| 5,660,985 A | 8/1997 | Pieken et al. | |
| 5,663,321 A | 9/1997 | Gmeiner et al. | |
| 5,741,900 A | 4/1998 | Gmeiner et al. | |
| 6,342,485 B1 | 1/2002 | Gmeiner | |
| 6,613,526 B2 | 9/2003 | Heilig et al. | |
| 6,699,843 B2 | 3/2004 | Pietras et al. | |
| 2004/0249130 A1 | 12/2004 | Stanton et al. | |
| 2005/0256071 A1* | 11/2005 | Davis | 514/44 |
| 2005/0282190 A1 | 12/2005 | Shi et al. | |
| 2005/0287128 A1* | 12/2005 | Guerciolini et al. | 424/93.21 |
| 2006/0088864 A1* | 4/2006 | Smolke et al. | 435/6 |
| 2006/0246123 A1 | 11/2006 | Gilboa et al. | |
| 2007/0009476 A1 | 1/2007 | Wilson et al. | |
| 2008/0026947 A1* | 1/2008 | Gmeiner | 506/4 |

FOREIGN PATENT DOCUMENTS

WO  WO 2009/046104 A1  4/2009
WO  WO2009046104  *  4/2009

OTHER PUBLICATIONS

Dollins CM et al. Assembling OX40 aptamers on a molecular scaffold to create a receptor-activating aptamer. Chemistry & Biology. 2008: 8 pp.
Wullner U et al. Cell-specific induction of apoptosis by rationally designed bivalent aptamer-siRNA transcripts silencing eukaryotic elongation factor 2. Current Cancer Drug Targets. 2008; 8(7): 554-565.
Santulli-Marotto S et al. Multivalent RNA aptamers that inhibit CTLA-4 and enhance tumor immunity. Cancer Research. Nov. 1, 2003; 63: 7483-7489.
Corrias et al., "Interaction of human plasma membrane proteins and oligodeoxynucleotides", *Biochemical Pharmacology*, 1998, 55: 1221-1227.
Farokhzad et al., "Nanoparticle-aptamer bioconjugates: a new approach for targeting prostate cancer cells", *Cancer Research*, 2004, 64: 7668-7672.
Fracasso et al., "Anti-tumor effects of toxins targeted to the prostate specific membrane antigen", *The Prostate*, 2002, 53: 9-23.
Gmeiner et al., "Enhanced DNA-Directed Effects of FdUMP[10] Compared to 5FU", *Nucleosides, Nucleotides & Nucleic Acids*, 2004, 23(1-2): 401-410.
U.S. Appl. No. 13/008,614, filed Jan. 18, 2011, William H. Gmeiner.
Gmeiner, William, "Novel Chemical Strategies for Thymidylate Synthase Inhibition", *Current Medicinal Chemistry*, 2005, 12: 191-202.
Liu et al., "Constitutive and Antibody-Induced Internalization of Prostate-specific Membrane Antigen", *Cancer Research*, 1981, 58: 4055-4060.
Liu et al., "Targeted drug delivery to chemoresistant cells: folic acid derivatization of fdUMP[10] enhances Cytotoxicity toward 5-FU-resistant human colorectal tumor cells", *The Journal of Organic Chemistry*, 2001, 66(17): 5655-5663.
Liu et al., "Efficacy and safety of FdUMP[10] in treatment of HT-29 human colon cancer xenografts", *Journal of Oncology*, 2002, 21: 303-308.
Loke et al., "Characterization of oligonucleotide transport into living cells", *Proceedings of the National Academy of Sciences*, 1989, 86: 3474-3478.
Longley et al., "5-Fluorouracil: Mechanisms of Action and Clinical Strategies", *Nature Publishing Group*, 2003, 3: 330-338.
Lupold et al., "Identification and Characterization of Nuclease-stabilized RNA Molecules that Bind Human Prostate Cancer Cells via the Prostate-specific Membrane Antigen", *Cancer Research*, 2002, 62: 4029-4033.
McNamara et al., "Multivalent 4-1BB binding aptamers costimulate CD8+ T cells and inhibit tumor growth in mice", *The Journal of Clinical Investigation*, 2008, 118(1): 376-386.
Morris et al., "High affinity ligands from in vitro selection: complex targets", *Proceedings of the National Academy of Sciences*, 1998, 95: 2902-2907.
Schulke et al., "The homodimer of prostate-specific membrane antigen is a functional target for cancer therapy", *PNAS*, 2003, 100(22): 12590-12595.
Zuker, Michael, "Mfold web server for nucleic acid folding and hybridization predication", *Nucleic Acids Research*, 2003, 31(13): 3406-3415.

* cited by examiner

*Primary Examiner* — Jennifer Pitrak McDonald
(74) *Attorney, Agent, or Firm* — Myers Bigel & Sibley, P.A.

(57) ABSTRACT

A compound of the formula A-B-C, is provided, wherein: A is a first nucleic acid that specifically binds to an extracellular surface protein expressed by a cell of interest, B is an alkyl linker; and C is a second nucleic acid that hybridizes to a complementary nucleic acid. In some embodiments, the first nucleic acid is an aptamer. In some embodiments, the nucleic acid comprises an active compound, particularly cytotoxic nucleotides such as poly-FdUMP. Compositions and methods of using such compounds for treating and/or detecting cancer are also described.

25 Claims, 6 Drawing Sheets

US 9,284,559 B2

MULTIVALENT APTAMER COMPLEXES

RELATED APPLICATIONS

This application claims the benefit of U.S. Provisional Patent Application Ser. No. 61/169,058, filed Apr. 14, 2009, the disclosure of which is incorporated by reference herein in its entirety.

GOVERNMENT SUPPORT

This invention was made with government support under grants from the Department of Defense and the National Institutes of Health. The government has certain rights to this invention.

FIELD OF INVENTION

The present invention concerns chemotherapeutic molecules and compositions thereof, and methods of use thereof for the treatment of cancer.

BACKGROUND OF THE INVENTION

Cancer is the second-leading cause of death in the United States and is a serious public health concern. The current generation of cytotoxic chemotherapeutic agents used for the treatment of cancer is not curative for a majority of patients. For many cancer patients, the use of chemotherapy extends patient-life by only a few months and often results in serious side effects that reduce the quality of life.

Anticancer drugs that are utilized for cancer chemotherapy include cytotoxic nucleoside analogs (Pratt et al., "Antimetabolites" in The Anticancer Drugs, $2^{nd}$ ed. Oxford University Press, New York. pp. 69-107 (1994)), such as analogs of the four nucleotides that are the principal components of DNA. Examples of cytotoxic analogs include the fluoropyrimidines (FPs) such as 5FU and FdU, which are analogs of Ura and dU, the precursor for dT, the arabinosyl nucleotides AraC and AraA, which are analogs of dC and dA, respectively, dFdC (gemcitabine), which is an analog of dC, and 6-mercaptopurine, which is an analog of dI, the precursor of dG.

SUMMARY OF THE INVENTION

A first aspect of the invention is a compound of the formula A-B-C, wherein: A is a first nucleic acid that specifically binds to an extracellular surface protein expressed by a cell of interest, B is an alkyl linker; and C is a second nucleic acid that hybridizes to a complementary nucleic acid. In some embodiments, the first nucleic acid is an aptamer. In some embodiments, the first nucleic acid is from 30 to 150 nucleotides in length. In some embodiments, the alkyl linker comprises C2-C6 loweralkyl. In some embodiments, the second nucleic acid is from 8 to 100 nucleotides in length. In some embodiments, the cell of interest is a cancer cell, microbial cell, or parasite cell. In some embodiments, the nucleic acid comprises an active compound, particularly cytotoxic nucleotides such as poly-FdUMP.

A second aspect of the present invention is a composition comprising a pair of compounds as described above and further herein, each member of the pair having a second nucleic acid that is complementary to and hybridized to the second nucleic acid of the other member of the pair. The composition may be provided in a pharmaceutically acceptable carrier.

A further aspect of the invention is the use of a composition as described above, and further herein, for treating and/or detecting cancer, or for the preparation of a medicament for treating and/or detecting cancer.

A further aspect of the invention is a method of introducing a nucleic acid of interest into a cell of interest, comprising contacting a composition as described above, and further herein, to the cell under conditions in which the nucleic acid of interest is internalized into the cell. In some embodiments the method is carried out in vitro; in other embodiments the method is carried out in vivo. For example, the cell of interest may be a cancer cell in a subject afflicted with cancer (e.g., prostate cancer), and the contacting is carried out by administering the composition to the subject in an amount effective to treat or detect the cancer.

DETAILED DESCRIPTION OF THE PREFERRED EMBODIMENTS

Figure 1:
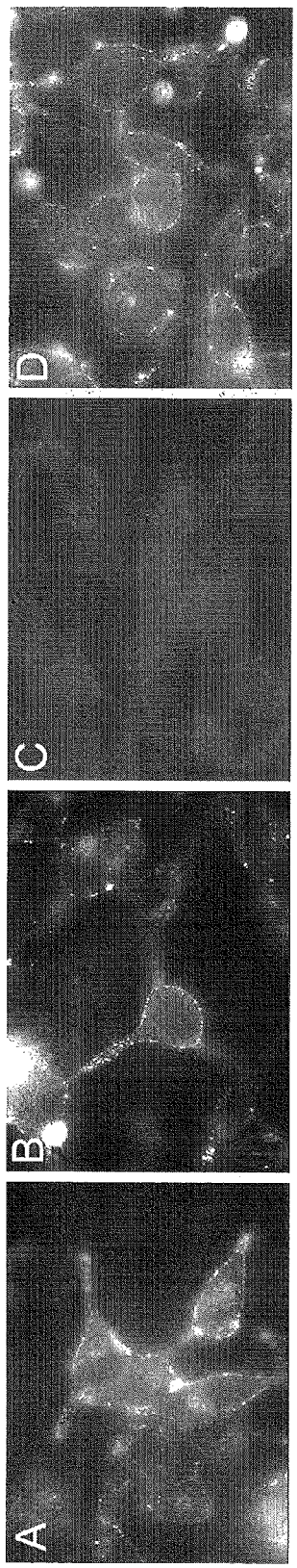
FIG. 1. Fluorescence microscopy images of the PSMA01 DNA aptamer binding to (A) C4-2 cells; (B) LNCaP cells; (C)PC3 cells. (D) Binding of the A10-3 RNA aptamer to C4-2 cells. Live cells were incubated in PBS with $1\times10^{-6}$ M Rhodamine-conjugated aptamer for 2 h at room temperature. Cells were fixed with 3.7% formaldehyde for 2 min prior to visualization using an Olympus inverted microscope.

The present invention is explained in greater detail below. This description is not intended to be a detailed catalog of all the different ways in which the invention may be implemented, or all of the features that may be added to the instant invention. For example, features illustrated with respect to one embodiment may be incorporated into other embodiments, and features illustrated with respect to a particular embodiment may be deleted from that embodiment. In addition, numerous variations and additions to the various embodiments suggested herein will be apparent to those skilled in the art in light of the instant disclosure which do not depart from the instant invention. Hence, the following specification is intended to illustrate some particular embodiments of the invention, and not to exhaustively specify all permutations, combinations and variations thereof.

As used in the description of the invention and the appended claims, the singular forms "a", "an" and "the" are intended to include the plural forms as well, unless the context clearly indicates otherwise. Furthermore, the term "about," as used herein when referring to a measurable value such as an amount of a compound, dose, time, temperature, and the like, is meant to encompass variations of 20%, 10%, 5%, 1%, 0.5%, or even 0.1% of the specified amount. Also, as used herein, "and/or" refers to and encompasses any and all possible combinations of one or more of the associated listed items, as well as the lack of combinations when interpreted in the alternative ("or").

The disclosures of all Patent references cited herein are incorporated herein by reference in their entirety.

1. Definitions

"Aptamer(s)" or "aptamer sequence(s)" as used herein are meant to refer to single stranded nucleic acids (RNA or DNA) whose distinct nucleotide sequence determines the folding of the molecule into a unique three dimensional structure. Aptamers comprising 15 to 120 nucleotides can be selected in vitro from a randomized pool of oligonucleotides ($10^{14}$-$10^{15}$ molecules). The "aptamers or aptamer sequences" comprise a sequence (sometimes a degenerate or random sequence), and can further comprise fixed sequences flanking that sequence. The term "aptamer" as used herein further contemplates the use of both native and modified DNA and RNA bases, e.g. beta-D-Glucosyl-Hydroxymethyluracil. See, e.g., U.S. Pat. No. 7,329,742.

"Detectable compounds" as used herein include, but are not limited to, radiolabels (e.g., $^{35}S$, $^{125}I$, $^{32}P$, $^{3}H$, $^{14}C$, $^{131}I$), enzyme labels (e.g., horseradish peroxidase, alkaline phosphatase), gold beads, chemiluminescence labels, ligands (e.g., biotin, digoxin) and/or fluorescence labels (e.g., rhodamine, phycoerythrin, fluorescein), a fluorescent protein including, but not limited to, green fluorescent protein or one of its many modified forms, a nucleic acid segment in accordance with known techniques, and energy absorbing and energy emitting agents.

"Active compound" as used herein includes, but is not limited to, cytotoxic nucleosides or nucleotides, antisense oligonucleotides, radionuclides, energy absorbing and energy emitting agents, and other cytotoxic agents. Other cytotoxic agents include, but are not limited to, ricin (or more particularly the ricin A chain), aclacinomycin, diphtheria toxin, Monensin, Verrucarin A, Abrin, Tricothecenes, and Pseudomonas exotoxin A, taxol, cytochalasin B, gramicidin D, ethidium bromide, emetine, mitomycin, etoposide, tenoposide, anti-mitotic agents such as the vinca alkaloids (e.g., vincristine and vinblastine), colchicin, anthracyclines such as doxorubicin and daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof, antimetabolites (e.g., methotrexate, 6-mercaptopurine, 6-thioguanine, cytarabine, and 5-fluorouracil decarbazine), alkylating agents (e.g., mechlorethamine, thioepa chlorambucil, melphalan, carmustine (BSNU), lomustine (CCNU), cyclothosphamide, busulfan, dibromomannitol, streptozotocin, mitomycin C, and cis-dichlorodiamine platinum (II) (DDP)), and antibiotics, including but not limited to, dactinomycin (formerly actinomycin), bleomycin, mithramycin, calicheamicin, and anthramycin (AMC).

"Cytotoxic nucleoside or nucleotide" as used herein includes, but is not limited to, 2',2'-difluorodeoxycytidine, (dFdC, gemcitabine), 5-fluorouracil (5-FU), 5-fluoro-2'-deoxyuridine-5'-O-monophosphate (FdUMP), 5-fluoro-2'-deoxyuridine (FdU), arabinosylcytosine (Ara-C), arabinosyl adenosine (Ara-A), fluorouracil arabinoside, mercaptopurine riboside, 5-aza-2'-deoxycytidine, arabinosyl 5-azacytosine, 6-azauridine, azaribine, 6-azacytidine, trifluoro-methyl-2'-deoxyuridine, thymidine, thioguanosine, 3-deazautidine, 2-Chloro-2'-deoxyadenosine (2-CdA), AZT (azidothymidine), 2',3'-dideoxyinosine (ddI), cytotoxic nucleoside-corticosteroid phosphodiester, 5-bromodeoxyuridine 5'-methylphosphonate, 5-fluorodeoxyuridine (FdUrd), fludarabine (2-F-ara-AMP), 6-mercaptopurine and 6-thioguanine, 2-chlorodeoxyadenosine (CdA), 2'-deoxycoformycin (pentostatin), 4'-thio-beta-D-arabinofuranosylcytosine, and any other cytotoxic dA, dC, dT, dG, dU, or homologs thereof.

"Antisense oligonucleotide," as used herein, refers to a nucleic acid that is complementary to and specifically hybridizes to a specified DNA or RNA sequence. Antisense oligonucleotide includes, but is not limited to, ribozymes, small interfering RNAs, short hairpin RNAs, micro RNAs, triplex-forming oligonucleotides, and/or PNAs. Antisense oligonucleotides and nucleic acids that encode the same can be made in accordance with conventional techniques. See, e.g., U.S. Pat. No. 5,023,243 to Tullis; U.S. Pat. No. 5,149,797 to Pederson et al. Those skilled in the art will appreciate that it is not necessary that the antisense oligonucleotide be fully complementary to a target sequence, as long as the degree of sequence similarity is sufficient for the antisense nucleotide sequence to specifically hybridize to its target and reduce production of the polypeptide (e.g., by at least about 30%, 40%, 50%, 60%, 70%, 80%, 90%, or 95% or more).

"Radionuclide" as described herein may be any radionuclide suitable for delivering a therapeutic dosage of radiation to a tumor or cancer cell, including, but not limited to, $^{225}$Ac, $^{227}$Ac, $^{211}$At, $^{131}$Ba, $^{77}$Br, $^{109}$Cd, $^{51}$Cr, $^{67}$Cu, $^{165}$Dy, $^{155}$Eu, $^{153}$Gd, $^{198}$Au, $^{166}$Ho, $^{113m}$In, $^{115m}$In, $^{123}$I, $^{125}$I, $^{131}$I, $^{189}$Ir, $^{191}$Ir, $^{192}$Ir, $^{194}$Ir, $^{52}$Fe, $^{55}$Fe, $^{59}$Fe, $^{177}$Lu, $^{109}$Pd, $^{32}$P, $^{226}$Ra, $^{186}$Re, $^{188}$Re, $^{153}$Sm, $^{46}$Sc, $^{47}$Sc, $^{72}$Se, $^{75}$Se, $^{105}$Ag, $^{89}$Sr, $^{35}$S, $^{177}$Ta, $^{117}$mSn, $^{121}$Sn, $^{166}$Yb, $^{169}$Yb, $^{90}$Y, $^{212}$Bi, $^{213}$Bi, $^{119}$Sb, $^{197}$Hg, $^{97}$Ru, $^{100}$Pd, $^{101m}$Rh, and $^{212}$Pb.

"Energy absorbing and energy emitting agent" as used herein includes, but is not limited to, diagnostic agents, contrast agents, iodinated agents, radiopharmaceuticals, fluorescent compounds and fluorescent compounds coencapsulated with a quencher, agents containing MRS/MRI sensitive nuclides, genetic material encoding contrast agents, and energy absorbing and heat emitting nanomaterials including, but not limited to, single-walled nanotubes and gold nanocages. Some examples of contrast agents include, but are not limited to, metal chelates, polychelates, multinuclear cluster complexes (U.S. Pat. No. 5,804,161), halogenated xanthene or a functional derivative of a halogenated xanthene (U.S. Pat. No. 6,986,740), gadolinium-diethylenetriaminepentaacetic acid (gadopentetate dimeglumine, GdDTPA; Magnavist), gadoteridol (ProHance), gadodiamide, gadoterate meglumine (Gd-DOTA), gadobenate dimeglumine (Gd-BOPTA/Dimeg; MultiHance), mangafodipir trisodium (Mn-DPDP), ferumoxides, paramagnetic analogue of doxorubicin, and ruboxyl (Rb). Some examples of iodinated agents include, but are not limited to, diatrizoate (3,5-di(acetamido)-2,4,6-triiodobenzoic acid), iodipamide (3,3'-adipoyl-diimino-di(2,4, 6-triiodobenzoic acid), acetrizoate [3-acetylamino-2,4,6-triiodobenzoic acid], aminotrizoate [3-amino-2,4,6-triiodobenzoic acid]), and iomeprol. Examples of radiopharmaceuticals include, but are not limited to, fluorine-18 fluorodeoxyglucose ([18F]FDG), Tc-99m Depreotide, carbon-11 hydroxyephedrine (HED), [18F]setoperone, [methyl-11C]thymidine, 99 mTc-hexamethyl propyleneamine oxime (HMPAO), 99 mTc-L, L-ethylcysteinate dimer (ECD), 99 mTc-sestamibi, thallium 201, I-131metaiodobenzylguanidine (MIBG), 123I-N-isopropyl-p-iodoamphetamine (IMP), 99 mTc-hexakis-2-methoxyisobutylisonitrile 99 mTc-tetrofosmin. Examples of agents containing MRS/MRI sensitive nuclides include, but are not limited to, perfluorocarbons and fluorodeoxyglucose. Examples of genetic material encoding contrast agents include, but are not limited to, paramagnetic reporter genes such as ferredoxin; paramagnetic tag(s) on liposomal lipids such as paramagnetic chelating groups added to PEG; detectable probes; and luciferin/luciferase reporter system.

"Nucleic acid" as used herein refers to single- or double-stranded molecules which may be deoxyribonucleic acid (DNA), ribonucleic acid (RNA), or homologs thereof such as peptide nucleic acid (PNA), which is comprised of stretches of nucleic acid polymers linked together by peptide linkers, or a combination thereof. The nucleic acid may represent a coding strand or its complement. The nucleic acids of this invention may be comprised of any combination of naturally-occurring nucleosides (A, G, C, T, U), and/or the nucleic acids may comprise nucleoside or nucleotide analogs and/or derivatives as are well known in the art, including cytotoxic, synthetic, rare, non-natural bases or altered nucleotide bases. A nucleic acid molecule in the form of a polymer of DNA may be comprised of one or more segments of cDNA, genomic DNA or synthetic DNA. In addition, a modification can be incorporated to reduce exonucleolytic degradation, such as a reverse (3'→5') linkage at the 3'-terminus.

"Cell of interest" as used herein may be any suitable cell, including but not limited to cancer cells, tissue cells generally (e.g., muscle, bone, nerve, liver, lung, etc.), pathological and non-pathological microbial cells (e.g., bacterial, mycobacterial, spirochetal rickettsial, chlamydial, mycoplasmal, and fungal, etc.), parasitic cells (e.g., protozoal, helminth, etc.), and plant cells, etc.

"Cancer cell" as used herein may be any cancer cell, including, but not limited to, lung, colon, ovarian, prostate, bone, nerve, liver, leukemia, and lymphoma cells.

"Bacterial cell" as used herein may be any bacterial cell including, but not limited to, Gram-negative bacteria, Gram-positive bacteria and other bacteria.

Examples of Gram-negative bacteria include, but are not limited to, bacteria of the genera, *Salmonella, Escherichia, Klebsiella, Haemophilus, Pseudomonas, Proteus, Neisseria, Vibro, Helicobacter, Brucella, Bordetella, Legionella, Campylobacter, Francisella, Pasteurella, Yersinia, Bartonella, Bacteroides, Streptobacillus, Spirillum, Moraxella* and *Shigella*. Furthermore, bacterial cell of interest includes Gram-negative bacteria including, but not limited to, *Escherichia coli, Pseudomonas aeruginosa, Neisseria meningitides, Neisseria gonorrhoeae, Salmonella typhimurium, Salmonella entertidis, Klebsiella pneumoniae, Haemophilus influenzae, Haemophilus ducreyi, Proteus mirabilis, Vibro cholera, Helicobacter pylori, Brucella abortis, Brucella melitensis, Brucella suis, Bordetella pertussis, Bordetella parapertussis, Legionella pneumophila, Campylobacter fetus, Campylobacter jejuni, Francisella tularensis, Pasteurella multocida, Yersinia pestis, Bartonella bacilliformis, Bacteroides fragilis, Bartonella henselae, Streptobacillus moniliformis, Spirillum minus, Moraxella catarrhalis (Branhamella catarrhalis),* and *Shigella dysenteriae*.

Examples of Gram-positive bacteria include, but are not limited to, bacteria of the genera *Listeria, Staphylococcus, Streptococcus, Bacillus, Corynebacterium, Peptostreptococcus,* and *Clostridium*. Furthermore, bacterial cell of interest includes Gram-positive bacteria including, but not limited to, *Listeria monocytogenes, Staphylococcus aureus, Streptococcus pyogenes, Streptococcus pneumoniae, Bacillus cereus, Bacillus anthracis, Clostridium botulinum, Clostridium perfringens, Clostridium difficile, Clostridium tetani, Corynebacterium diphtherias, Corynebacterium ulcerans,* and *Peptostreptococcus anaerobius*.

Additional bacteria include bacterial genera including, but not limited to, *Actinomyces, Propionibacterium, Nocardia* and *Streptomyces*. Furthermore, bacterial cell of interest of the present invention includes, but is not limited to, *Actinomyces israeli, Actinomyces gerencseriae, Actinomyces viscosus, Actinomyces naeslundii, Propionibacterium propionicus, Nocardia asteroides, Nocardia brasiliensis, Nocardia otitidiscaviarum* and *Streptomyces somaliensis*.

"Mycobacterial cell" as used herein may be any mycobacterial cell, including but not limited to mycobacteria belonging to the mycobacteria families including, but not limited to, Mycobacteriaceae. Additionally, mycobacterial cell of the present invention includes, but is not limited to, *Mycobacterium tuberculosis, Mycobacterium leprae, Mycobacterium avium-intracellulare, Mycobacterium kansasii,* and *Mycobacterium ulcerans*.

"Spirochetal cell" as used herein may be any spirochetal cell, including but not limited to spirochetes belonging to the genera including, but not limited to, *Treponema, Leptospira*, and *Borrelia*. Additionally, spirochetal cell of the present invention includes, but is not limited to, *Treponema palladium, Treponema pertenue, Treponema carateum, Leptospira interrogans, Borrelia burgdorferi*, and *Borrelia recurrentis*.

"Rickettsial cell" as used herein may be any rickettsial cell, including but not limited to *rickettsia* belonging to the genera including, but not limited to, *Rickettsia, Ehrlichia, Orienta, Bartonella* and *Coxiella*. Furthermore, rickettsial cell includes, but is not limited to, *Rickettsia rickettsii, Rickettsia akari, Rickettsia prowazekii, Rickettsia typhi, Rickettsia conorii, Rickettsia sibirica, Rickettsia australis, Rickettsia japonica, Ehrlichia chaffeensis, Orienta tsutsugamushi, Bartonella quintana*, and *Coxiella burni*.

"Chlamydial cell" as used herein may be any chlamydial cell belonging to the genera including, but not limited to, *Chlamydia*. Furthermore, chlamydial cell of the present invention includes, but is not limited to, *Chlamydia trachomatis, Chlamydia caviae, Chlamydia pneumoniae, Chlamydia muridarum, Chlamydia psittaci*, and *Chlamydia pecorum*.

"Mycoplasmal cell" as used herein may be any mycoplasmal cell belonging to the genera including, but not limited to, *Mycoplasma* and *Ureaplasma*. In addition, mycoplasmal cell includes but is not limited to, *Mycoplasma pneumoniae, Mycoplasma hominis, Mycoplasma genitalium*, and *Ureaplasma urealyticum*.

"Fungal cell" as used herein may be any fungal cell belonging to the genera including, but not limited to, *Aspergillus, Candida, Cryptococcus, Coccidioides, Tinea, Sporothrix, Blastomyces, Histoplasma, Pneumocystis* and *Saccharomyces*. Additionally, fungal cell of the present invention includes, but is not limited to, *Aspergillus fumigatus, Aspergillus flavus, Aspergillus niger, Aspergillus terreus, Aspergillus nidulans, Candida albicans, Coccidioides immitis, Cryptococcus neoformans, Tinea unguium, Tinea corporis, Tinea cruris, Sporothrix schenckii, Blastomyces dermatitidis, Histoplasma capsulatum, Histoplasma duboisii*, and *Saccharomyces cerevisiae*.

"Parasitic cell" as used herein may include any parasitic cell belonging to the genera including, but not limited to, *Entamoeba, Dientamoeba, Giardia, Balantidium, Trichomonas, Cryptosporidium, Isospora, Plasmodium, Leishmania, Trypanosoma, Babesia, Naegleria, Acanthamoeba, Balamuthia, Enterobius, Strongyloides, Ascaradia, Trichuris, Necator, Ancylostoma, Uncinaria, Onchocerca, Mesocestoides, Echinococcus, Taenia, Diphylobothrium, Hymenolepsis, Moniezia, Dicytocaulus, Dirofilaria, Wuchereria, Brugia, Toxocara, Rhabditida, Spirurida, Dicrocoelium, Clonorchis, Echinostoma, Fasciola, Fascioloides, Opisthorchis, Paragonimus*, and *Schistosoma*. Additionally, parasitic cell of the present invention includes, but is not limited to, *Entamoeba histolytica, Dientamoeba fragilis, Giardia lamblia, Balantidium coli, Trichomonas vaginalis, Cryptosporidium parvum, Isospora belli, Plasmodium malariae, Plasmodium ovale, Plasmodium falciparum, Plasmodium vivax, Leishmania braziliensis, Leishmania donovani, Leishmania tropica, Trypanosoma cruzi, Trypanosoma brucei, Babesia divergens, Babesia microti, Naegleria fowleri, Acanthamoeba culbertsoni, Acanthamoeba polyphaga, Acanthamoeba castellanii, Acanthamoeba astronyxis, Acanthamoeba hatchetti, Acanthamoeba rhysodes, Balamuthia mandrillaris, Enterobius vermicularis, Strongyloides stercoralis, Strongyloides fulleborni, Ascaris lumbricoides, Trichuris trichiura, Necator americanus, Ancylostoma duodenale, Ancylostoma ceylanicum, Ancylostoma braziliense, Ancylostoma caninum, Uncinaria stenocephala, Onchocerca volvulus, Mesocestoides variabilis, Echinococcus granulosus, Taenia solium, Diphylobothrium latum, Hymenolepis nana, Hymenolepis diminuta, Moniezia expansa, Moniezia benedeni, Dicytocaulus viviparous, Dicytocaulus filarial, Dicytocaulus arnfieldi, Dirofilaria repens, Dirofilaria immitis, Wuchereria bancrofti, Brugia malayi, Toxocara canis, Toxocara cati, Dicrocoelium dendriticum, Clonorchis sinensis, Echinostoma, Echinostoma ilocanum, Echinostoma jassyenese, Echinostoma malayanum, Echinostoma caproni, Fasciola hepatica, Fasciola gigantica, Fascioloides magna, Opisthorchis viverrini, Opisthorchis felineus, Opisthorchis sinensis, Paragonimus westermani, Schistosoma japonicum, Schistosoma mansoni, Schistosoma haematobium* and *Schistosoma haematobium*.

"Extracellular surface protein" as used herein may be any extracellular surface protein including, but not limited to, growth factor receptors, receptor tyrosine kinases, folate hydrolases, GPI-anchored cell surface antigens, pumps, and cell surface receptors including, but not limited to, G-protein coupled receptors, ion channel-linked receptors, and enzyme-linked receptors. Extracellular surface proteins of interest may be those "differentially expressed" by a targeted cell of interest, in comparison to a cell that is not to be targeted by a cytotoxic nucleotide. For example, the cancer cells differ from normal cells in many respects, including the up- or down-regulation of numerous genes. Among the genes that are differentially regulated in cancer cells are genes that encode proteins that are expressed on the extracellular surface. As an example, specific proteins are expressed on the extracellular surface of prostate cancer (PC) cells that are not expressed (or are expressed at very low levels) by normal prostatic epithelial cells and cells from other normal tissues. Extracellular proteins that are expressed exclusively by PC cells are excellent candidates for specific targeting of malignant cells with anticancer drugs. Cytotoxic oligodeoxynucleotides (ODNs) may be internalized by malignant cells that express specific ODN receptor proteins (Corrias et al., Biochem. Pharmacol. 55: 1221-1227 (1998)). The expression of prostate specific membrane antigen (PSMA) is limited to PC cells and cells of the tumor neovasculature (Schulke et al., Proc. Natl. Acad. Sci. USA 100: 12590-12595 (2003)). A second protein that displays characteristics suitable for developing targeted therapeutics for PC is prostate stem cell antigen (PSCA; Saffran et al., Proc. Natl. Acad. Sci. USA 98: 2658-2663 (2001)).

In one embodiment, extracellular proteins that form dimers are preferred. Examples include, but are not limited to, PSMA and transferrin receptor.

In another embodiment, extracellular proteins that are associated with the development of tumor neovasculature are preferred. PSMA is a non-limiting example thereof.

"Viral disease" as used herein includes, but is not limited to, those caused by viruses belonging to the viral families including, but not limited to, Flaviviridae, Arenaviradae, Bunyaviridae, Filoviridae, Poxyiridae, Togaviridae, Paramyxoviridae, Herpesviridae, Picornaviridae, Caliciviridae, Reoviridae, Rhabdoviridae, Papovaviridae, Parvoviridae, Adenoviridae, Hepadnaviridae, Coronaviridae, Retroviridae, and Orthomyxoviridae. Furthermore, viral diseases that can be treated using the compounds of the present invention can be caused by the viruses including, but not limited to, Yellow fever virus, St. Louis encephalitis virus, Dengue virus, Hepatitis G virus, Hepatitis C virus, Bovine diarrhea virus, West Nile virus, Japanese B encephalitis virus, Murray Valley encephalitis virus, Central European tick-borne encephalitis virus, Far eastern tick-born encephalitis virus, Kyasanur forest virus, Louping ill virus, Powassan virus, Omsk hemorrhagic fever virus, Kumilinge virus, Absetarov anzalova hypr virus, Ilheus virus, Rocio encephalitis virus, Langat virus, Lymphocytic choriomeningitis virus, Junin virus, Bolivian hemorrhagic fever virus, Lassa fever virus, California encephalitis virus, Hantaan virus, Nairobi sheep disease virus, Bunyamwera virus, Sandfly fever virus, Rift valley fever virus, Crimean-Congo hemorrhagic fever virus, Marburg virus, Ebola virus, Variola virus, Monkeypox virus, Vaccinia virus, Cowpox virus, Orf virus, Pseudocowpox virus, Molluscum contagiosum virus, Yaba monkey tumor virus, Tanapox virus, Raccoonpox virus, Camelpox virus, Mousepox virus, Tanterapox virus, Volepox virus, Buffalopox virus, Rabbitpox virus, Uasin gishu disease virus, Sealpox virus, Bovine papular stomatitis virus, Camel contagious eethyma virus, Chamios contagious eethyma virus, Red squirrel parapox virus, Juncopox virus, Pigeonpox virus, Psittacinepox virus, Quailpox virus, Sparrowpox virus, Starlingpox virus, Peacockpox virus, Penguinpox virus, Mynahpox virus, Sheeppox virus, Goatpox virus, Lumpy skin disease virus, Myxoma virus, Hare fibroma virus, Fibroma virus, Squirrel fibroma virus, Malignant rabbit fibroma virus, Swinepox virus, Yaba-like disease virus, Albatrosspox virus, Cotia virus, Embu virus, Marmosetpox virus, Marsupialpox virus, Mule deer poxvirus virus, Volepox virus, Skunkpox virus, Rubella virus, Eastern equine encephalitis virus, Western equine encephalitis virus, Venezuelan equine encephalitis virus, Sindbis virus, Semliki forest virus, Chikungunya virus, O'nyong-nyong virus, Ross river virus, Parainfluenza virus, Mumps virus, Measles virus (rubeola virus), Respiratory syncytial virus, Herpes simplex virus type 1, Herpes simplex virus type 2, Varicella-zoster virus, Epstein-Barr virus, Cytomegalovirus, Human b-lymphotrophic virus, Human herpesvirus 7, Human herpesvirus 8, Poliovirus, Coxsackie A virus, Coxsackie B virus, ECHOvirus, Rhinovirus, Hepatitis A virus, Mengovirus, ME virus, Encephalomyocarditis (EMC) virus, MM virus, Columbia SK virus, Norwalk agent, Hepatitis E virus, Colorado tick fever virus, Rotavirus, Vesicular stomatitis virus, Rabies virus, Papilloma virus, BK virus, JC virus, B19 virus, Adeno-associated virus, Adenovirus, serotypes 3,7,14,21, Adenovirus, serotypes 11,21, Adenovirus, Hepatitis B virus, Coronavirus, Human T-cell lymphotrophic virus, Human immunodeficiency virus, Human foamy virus, Influenza viruses, types A, B, C, and Thogotovirus.

"Treat" or "treatment" as used herein refers to an action resulting in a reduction in the severity of the subject's condition, wherein the condition is at least partially improved or ameliorated, and/or there is some alleviation, mitigation or decrease in at least one clinical symptom (or agricultural index for plants), and/or there is a delay in the progression of the condition, and/or prevention or delay of the onset of the condition. Thus, the term "treat" refers to both prophylactic and therapeutic treatment regimes. Compounds generated by the methods of the present invention may be used for the diagnosis and/or treatment of human subjects, or animal subjects for veterinary or drug development purposes. Examples of animal subjects include mammalian (e.g., dog, cat, mouse, rat, horse, cow, pig, sheep, etc.), reptile, amphibian, and avian (e.g., parrot, budgie, chicken, turkey, duck, geese, quail, pheasant) subjects.

2. Active Compounds

In general, compounds (sometimes also referred to as "active compounds" herein) are compounds of the general formula A-B-C, wherein:

A is a first nucleic acid that specifically binds to an extracellular surface protein expressed by a cell of interest, B is an alkyl linker; and C is a second nucleic acid that hybridizes to a complementary nucleic acid. Each of these is discussed in further detail below.

A. First Nucleic Acid.

The first nucleic acid is, in general, selected to specifically bind to an extracellular surface protein expressed by a cell of interest. The first nucleic acid optionally but preferably contains cytotoxic nucleotides. Numerous such nucleic acids, including those sometimes referred to as "aptamers", are known or can be identified in accordance with known techniques, such as described in William H. Gmeiner, Cytotoxic nucleotides for targeted therapeutics, US Patent Application 20080026947 (published Jan. 31, 2008). Other methods of identifying nucleic acids that can be used as the first nucleic acid herein include but are not limited to those described in U.S. Pat. Nos. 7,329,742; 7,312,325; 6,867,289; 6,858,390; and 6,369,208, or variations thereof that will be apparent to those skilled in the art given the present disclosure.

In general, an aptamer would be selected as a species of a nucleic acid pool, and then synthetically resynthesized in whole or in part to provide active compounds. As such, the elements of the aptamer will depend upon the features of the nucleic acid with the pool from which the aptamer is produced. In some embodiments, the size of the nucleic acids species within the pool can be in a range of about 30 nucleotides to about 150 nucleotides. In preferred embodiments, the nucleic acid species of the present invention comprises three regions: a "random" region flanked by two "constant" regions. It should be noted while the sequence in this region is random during the course of SELEX or other procedure to identify sequences that have the desired characteristics (e.g. binding to extracellular protein) these sequences are not random, but selected for in the course of practicing the invention. The two "constant" regions need not be identical to each other, but comprise known nucleotide sequences. These "constant" regions are used for the annealing of PCR primers during PCR amplification. The lengths of the "constant" regions can be in a range of about 8 nucleotides to about 35 nucleotides. In some embodiments the lengths of the "constant" regions are in a range of about 12 nucleotides to about 22 nucleotides. The length of the constant regions need not be the same as one another, and indeed each region may be modified in length and/or sequence based on folding predictions or results following the identification of optimal "random" regions. The "random" region of the nucleic acids species within the pool consists of random arrangements of nucleotide sequences. The length of the "random" region is not critical, but in general can be from 10 or 20 nucleotides in length up to 80 or 100 nucleotides in length, or more.

Synthesizing a nucleic acid having a sequence corresponding to a selected nucleic acid and incorporating a compound of interest may done according to any method standard in the art including, but not limited to, de novo chemical synthesis of polynucleotides, such as by presently available automated DNA synthesizers, and standard phosphoramidite chemistry. De novo chemical synthesis of a polynucleotide can be conducted using any suitable method, including, but not limited to, the phosphotriester or phosphodiester methods. See Narang et al., *Meth. Enzymol.*, 68:90 (1979); U.S. Pat. No. 4,356,270; Itakura et al., *Ann. Rev. Biochem.*, 53:323-56 (1989); Brown et al., *Meth. Enzymol.*, 68:109 (1979); and U.S. Pat. No. 6,911,310 issued to Heller. In one embodiment of the present invention, automated nucleic acid synthesis is conducted using an Applied Biosystem 394™ automated DNA/RNA synthesizer (Applied Biosystems, Foster City, Calif.).

B. Alkyl Linkers.

Alkyl linkers (also referred to as alkyl spacers) may for example be partially saturated or fully saturated C2-C6 or C10 alkyl groups, which can be linear or branched and may optionally contain one or more hetero atoms (e.g., one, two, three or four heteroatoms selected from N, O, and S), as long as their is at least one alkyl bond, —CH$_2$—CH$_2$—, in the main chain between the two linked groups (though in some preferred embodiments, heteroatoms are excluded therefrom). Alkyl linkers include groups of the formula —X—Y—Z—, where X and Y may be present or absent; at least one of X, Y, and Z is an alkyl group of the formula —[CH$_2$]$_n$— where n is an integer of from 1, 2 or 3 up to 5 or 10; and otherwise each of X, Y, and Z can be selected from the group consisting of alkenyl, alkynyl, alkoxy, etc. The linker may be of any suitable length, for example, 10, 20 or 50 Angstroms in length, up to 100, 200 or 500 Angstroms in length, or more.

Alkyl linkers suitable for phosphoramidite synthesis of nucleic acids are known and available. A currently preferred example is 3-(4,4'-Dimethoxytrityloxy)propyl-1-[(2-cyanoethyl)-(N,N-diisopropyl)]-phosphoramidite, commercially available as Spacer Phosphoramidite C3 (Product No. 10-1913-xx) from Glen Research Corporation, 22825 Davis Drive, Sterling, Va. 20164 USA.

C. Second Nucleic Acid.

The second nucleic acid (which optionally but preferably contains cytotoxic nucleotides) can be of any suitable length to provide hybridization to another nucleic acid, according to the well-known principles of Watson-Crick pairing. In general, the second nucleic acid can be of from 5 or 10 to 40 or 60 nucleotides in length, or more. Depending upon how the alkyl linker is synthesized in the molecule, the second nucleic acid can be continuously synthesized onto the growing polymer molecule in a continuous automated fashion, or synthesized separately and then covalently coupled to other portions of the molecule. Flexible linkers as described above can optionally be included in the second nucleic acid.

D. Additional Features.

To aid in detection, the at least one nucleic acid from the first subpopulation may be labeled with a detectable label using methods standard in the art, wherein the detectable label can include, but is not limited to, fluorescent dyes, fluorophores, chromophores, affinity labels, metal chelates, chemically reactive groups, enzymes, radionuclides, electrochemically detectable moieties, and energy absorbing or energy emitting compounds.

Fluorescent dyes that can be used with the present invention are any capable of binding to nucleic acids as defined herein and include, but are not limited to, the coumarin dyes, acetyl azide, fluorescein isothiocyanate, 1,2-dihexadecanoyl-sn-glycero-3-phosphoethanolamine, 8-(6-aminohexyl) amino adenosine 3',5'-cyclicmonophosphate, bis(triethylammonium) salt, rhodamine dyes, sulfonyl chloride, CyDye™ flors, and carboxynaphtofluorescein. The haptenes that may be used for labeling include, but are not limited to, biotin, digoxigenin, and 2,4-dinitrophenyl. The haptenes require fluorescently-labeled antibodies or specific proteins for visualization/detection.

Labeling of nucleic acids with electrophore mass labels is described, for example, in Xu et al., J. Chromatography 764: 95-102 (1997). Electrophores are compounds that can be detected with high sensitivity by electron capture mass spectrometry (EC-MS). Electrophore mass labels can be attached to a probe using chemistry that is well known in the art for reversibly modifying a nucleotide (e.g., well-known nucleotide synthesis chemistry teaches a variety of methods for attaching molecules to nucleotides as protecting groups). Electrophore mass labels are detected using a variety of well-known electron capture mass spectrometry devices. Further, techniques that may be used in the detection of electrophore mass labels include, for example, fast atomic bombardment mass spectrometry (See Koster et al., Biomedical Environ. Mass Spec. 14:111-116 (1987)); plasma desorption mass spectrometry; electrospray/ionspray (See Fenn et al., J. Phys. Chem. 88:4451-59 (1984), PCT Appln. No. WO 90/14148, Smith et al., Anal. Chem. 62:882-89 (1990)); and matrix-assisted laser desorption/ionization (Hillenkamp et al. *Biological Mass Spectrometry* (Burlingame and McCloskey, eds.), Elsevier Science Pub., Amsterdam, pp. 49-60, 1990); Huth-Fehre et al., *Rapid Communications in Mass Spectrometry*, 6:209-13 (1992)). (See also U.S. Pat. No. 6,979,548 issued to Ford et al.)

Methods for conjugation of detectable labels to nucleic acids are well known in the art, for example, Schubert et al., *Nucleic Acids Research* 18:3427 (1990) Smith et al., *Nature*, 321:674-679 (1986); Agarawal et al., *Nucleic Acids Research*, 14:6227-6245 (1986); Chu et al., *Nucleic Acids Research*, 16:3671-3691 (1988).

In some embodiments, modified oligonucleotides incorporate activated anticancer drugs into three-dimensional nucleic acid structures that selectively bind to and are internalized by cancer cells. Modified oligonucleotides are comprised, in part, of relatively low molecular weight activated drugs. Thus, the three-dimensional structures of modified oligonucleotides that facilitate selective binding to and penetration of targeted cells are formed based upon the chemical and structural properties of the component drugs or cytotoxic nucleotides. In preferred embodiments, the activated drug is 5-fluoro-2'-deoxyuridine-5'-O-monophosphate (FdUMP).

Incorporation of a compound of interest into a selected nucleic acid sequence requires that the selected nucleic acid sequence retains its original three-dimensional structure of the native sequence following the incorporation. In some embodiments, folding calculations are performed to compare the predicted folding patterns of the chemical structure of the native nucleic acid sequence with that of a nucleic acid sequence incorporating one or more compound of interest. Calculations can be performed with, e.g., folding programs such as mFOLD (Michael Zuker, Burnet Institute). Such calculations apply an algorithm to the native sequence of the nucleic acid to determine folding patterns that yield the most stable secondary structures. This approach provides insight into the likely location of double helical regions that occur within the three-dimensional structure of the nucleic acid. The structural characteristics of the native and modified nucleic acids can also be determined using circular dichroism (CD) spectroscopy and ultraviolet (UV) hyperchromicity measurements. Other methods of comparison will be apparent to those skilled in the art. Preferred nucleic acids of interest are those that incorporate compounds of interest in such a way as to not significantly alter the folding characteristics of the native sequences.

In some embodiments, modified nucleic acids are further evaluated for the extent to which they selectively kill cells of interest, e.g., through the release of cytotoxic nucleotides by 3'-O-exonucleolytic degradation. Cell viability can be evaluated, e.g., using 3-(4,5-dimethylhiazole-2-yl)-5-(3-carboxymethoxyphenyl)-2-(4-sulfophenyl)-2H-tetrazolium, inner salt (MTS) assays. Preferred nucleic acids are those that are cytotoxic towards cells of interest and not cytotoxic to non-targeted cells.

In some embodiments of the present invention, a synthetic nucleic acid may comprise one compound of interest. In other embodiments, a synthetic nucleic acid may incorporate more than one compound of interest. In some embodiments, one of the compounds of interest incorporated into the synthetic nucleic acid may be a detectable compound, and/or an active compound.

In preferred embodiments, cytotoxic oligodeoxynucleotides are oligodeoxynucleotides (ODNs) that contain one or more cytotoxic nucleoside analogs. Once incorporated into an ODN, the 5'-O-monophosphate form of the nucleoside is present as an intact unit that is embedded in the ODN polymer. The cytotoxic nucleoside analogs may be incorporated as a stretch of several ODNs, or may be incorporated at various places in the nucleotide species. In some embodiments, cytotoxic ODNs are arranged as a stretch of 2, 3, 4, or 5 to 20, 25, 30, or 40 ODNs. A preferred example of a cytotoxic ODN is FdUMP[10], a linear homopolymer of FdUMP, the thymidylate synthase inhibitory metabolite of the anticancer drug 5-fluorouracil (5FU). (Gmeiner, Curr. Med. Chem. 12: 1345-1359 (2005); Gmeiner et al., Nucl. Nuct. Nucl. Acids 23: 401-410 (2004)). Another preferred example is FdUMP[5]. The cytotoxic ODNs may be included in the synthesis of a desired nucleotide species, or may be appended to a desired nucleotide species. Synthesis and toxicity of FdUMP are found in U.S. Pat. No. 5,457,187 (Gmeiner et al.); U.S. Pat. No. 5,614,505 (Gmeiner et al.); U.S. Pat. No. 5,663,321 (Gmeiner et al.); U.S. Pat. No. 5,741,900 (Gmeiner et al.); and U.S. Pat. No. 6,342,485 (Gmeiner).

In some embodiments, ODNs may be synthesized to incorporate compounds of interest such as cytotoxic nucleoside analogs, either before or after the enrichment selections of candidate ODN sequences. In a preferred embodiment, ODNs selected in the first and second pools do not comprise a compound of interest. The selected ODNs are sequenced and analyzed to determine whether the incorporation of a compound on interest will affect their activity towards a biological target of interest. Cytotoxic ODNs are then subsequently synthesized consistent with analysis predictions (e.g. predicted folding). However, synthesis of ODNs containing a compound on interest such as a cytotoxic nucleoside analog may also be performed prior to the enrichment steps.

Modified ODNs of the present invention can be optimized, e.g., for treatment of PC and other malignancies. In some embodiments of the present invention, the modified ODNs target xPSM using FdUMP as the active drug. In other embodiments, the modified ODNs target extracellular surface proteins that are differentially expressed specifically on the surface of certain PC cells (e.g. prostate stem cell antigen). In further embodiments the modified ODNs administered to a particular patient may be customized to reflect the protein profile expressed by a specific patient. Additionally, the choice of drugs for inclusion into the modified ODN structure may be expanded to reflect the drug-profile that provides the maximum response for a particular malignancy. The ODNs of the present invention are compatible with a wide-range of cytotoxic compounds, including, but not limited to, nucleoside analogs, cytotoxic drugs, radionuclides, modifiers of gene expression and nanoparticles.

3. Compositions and Formulations

Initially, a pair of active compounds of the present invention, as described above, are hybridized to one another in accordance with well-known techniques (e.g., simply mixing together in an aqueous solution, or annealing by gentle heating and cooling in accordance with known techniques) to produce a hybridized composition. They hybridized composition is, for convenience, sometimes also referred to as an "active compound" herein.

The active compounds described above may be formulated for administration in a pharmaceutical carrier in accordance with known techniques. See, e.g., Remington, *The Science And Practice of Pharmacy* ($9^{th}$ Ed. 1995). In the manufacture of a pharmaceutical formulation according to the invention, the active compound (including the physiologically acceptable salts thereof) is typically admixed with, inter alia, an acceptable carrier. The carrier must, of course, be acceptable in the sense of being compatible with any other ingredients in the formulation and must not be deleterious to the patient. The carrier may be a solid or a liquid, or both, and is preferably formulated with the compound as a unit-dose formulation, for example, a tablet, which may contain from 0.01 or 0.5% to 95% or 99% by weight of the active compound. One or more active compounds may be incorporated in the formulations of the invention, which may be prepared by any of the well known techniques of pharmacy comprising admixing the components, optionally including one or more accessory ingredients.

The formulations of the invention include those suitable for oral, rectal, topical, buccal (e.g., sub-lingual), vaginal, parenteral (e.g., subcutaneous, intramuscular, intradermal, or intravenous), topical (i.e., both skin and mucosal surfaces, including airway surfaces) and transdermal administration, although the most suitable route in any given case will depend on the nature and severity of the condition being treated and on the nature of the particular active compound which is being used.

Formulations suitable for oral administration may be presented in discrete units, such as capsules, cachets, lozenges, or tablets, each containing a predetermined amount of the active compound; as a powder or granules; as a solution or a suspension in an aqueous or non-aqueous liquid; or as an oil-in-water or water-in-oil emulsion. Such formulations may be prepared by any suitable method of pharmacy which includes the step of bringing into association the active compound and a suitable carrier (which may contain one or more accessory ingredients as noted above). In general, the formulations of the invention are prepared by uniformly and intimately admixing the active compound with a liquid or finely divided solid carrier, or both, and then, if necessary, shaping the resulting mixture. For example, a tablet may be prepared by compressing or molding a powder or granules containing the active compound, optionally with one or more accessory ingredients. Compressed tablets may be prepared by compressing, in a suitable machine, the compound in a free-flowing form, such as a powder or granules optionally mixed with a binder, lubricant, inert diluent, and/or surface active/dispersing agent(s). Molded tablets may be made by molding, in a suitable machine, the powdered compound moistened with an inert liquid binder.

Formulations suitable for buccal (sub-lingual) administration include lozenges comprising the active compound in a flavoured base, usually sucrose and acacia or tragacanth; and pastilles comprising the compound in an inert base such as gelatin and glycerin or sucrose and acacia.

Formulations of the present invention suitable for parenteral administration comprise sterile aqueous and non-aqueous injection solutions of the active compound(s), which preparations are preferably isotonic with the blood of the intended recipient. These preparations may contain anti-oxidants, buffers, bacteriostats and solutes which render the formulation isotonic with the blood of the intended recipient. Aqueous and non-aqueous sterile suspensions may include suspending agents and thickening agents. The formulations may be presented in unit\dose or multi-dose containers, for example sealed ampoules and vials, and may be stored in a freeze-dried (lyophilized) condition requiring only the addition of the sterile liquid carrier, for example, saline or water-for-injection immediately prior to use. Extemporaneous injection solutions and suspensions may be prepared from sterile powders, granules and tablets of the kind previously described. For example, in one aspect of the present invention, there is provided an injectable, stable, sterile composition comprising an active compound(s), or a salt thereof, in a unit dosage form in a sealed container. The compound or salt is provided in the form of a lyophilizate which is capable of being reconstituted with a suitable pharmaceutically acceptable carrier to form a liquid composition suitable for injection thereof into a subject. The unit dosage form typically comprises from about 10 mg to about 10 grams of the compound or salt. When the compound or salt is substantially water-insoluble, a sufficient amount of emulsifying agent which is physiologically acceptable may be employed in sufficient quantity to emulsify the compound or salt in an aqueous carrier. One such useful emulsifying agent is phosphatidyl choline.

Formulations suitable for rectal administration are preferably presented as unit dose suppositories. These may be prepared by admixing the active compound with one or more conventional solid carriers, for example, cocoa butter, and then shaping the resulting mixture.

Formulations suitable for topical application to the skin preferably take the form of an ointment, cream, lotion, paste, gel, spray, aerosol, or oil. Carriers which may be used include petroleum jelly, lanoline, polyethylene glycols, alcohols, transdermal enhancers, and combinations of two or more thereof.

Formulations suitable for transdermal administration may be presented as discrete patches adapted to remain in intimate contact with the epidermis of the recipient for a prolonged period of time. Formulations suitable for transdermal administration may also be delivered by iontophoresis (see, for example, *Pharmaceutical Research* 3 (6):318 (1986)) and typically take the form of an optionally buffered aqueous solution of the active compound. Suitable formulations comprise citrate or bis\tris buffer (pH 6) or ethanol/water and contain from 0.1 to 0.2M active ingredient.

Further, the present invention provides liposomal formulations of the compounds disclosed herein and salts thereof. The technology for forming liposomal suspensions is well known in the art. When the compound or salt thereof is an aqueous-soluble salt, using conventional liposome technology, the same may be incorporated into lipid vesicles. In such an instance, due to the water solubility of the compound or salt, the compound or salt will be substantially entrained within the hydrophilic center or core of the liposomes. The lipid layer employed may be of any conventional composition and may either contain cholesterol or may be cholesterol-free. When the compound or salt of interest is water-insoluble, again employing conventional liposome formation technology, the salt may be substantially entrained within the hydrophobic lipid bilayer which forms the structure of the liposome. In either instance, the liposomes which are produced may be reduced in size, as through the use of standard sonication and homogenization techniques.

Of course, the liposomal formulations containing the compounds disclosed herein or salts thereof, may be lyophilized to produce a lyophilizate which may be reconstituted with a pharmaceutically acceptable carrier, such as water, to regenerate a liposomal suspension.

Other pharmaceutical compositions may be prepared from the water-insoluble compounds disclosed herein, or salts thereof, such as aqueous base emulsions. In such an instance, the composition will contain a sufficient amount of pharmaceutically acceptable emulsifying agent to emulsify the desired amount of the compound or salt thereof. Particularly useful emulsifying agents include phosphatidyl cholines, and lecithin.

In addition to active compound(s), the pharmaceutical compositions may contain other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate. Further, the compositions may contain microbial preservatives. Useful microbial preservatives include methylparaben, propylparaben, and benzyl alcohol. The microbial preservative is typically employed when the formulation is placed in a vial designed for multidose use. Of course, as indicated, the pharmaceutical compositions of the present invention may be lyophilized using techniques well known in the art.

4. Use

As noted above, compounds of the present invention may be used to detect and/or selectively kill or inhibit the growth of cells of interest, including but not limited to cancer cells, tissue cells generally (e.g., muscle, bone, nerve, liver, lung, etc.), pathological and non-pathological microbial cells (e.g., bacterial, mycobacterial, spirochetal rickettsial, chlamydial, mycoplasmal, and fungal, etc.), parasitic cells (e.g., protozoal, helminth, etc.), and plant cells, etc. Such methods may be carried out in vitro or in vivo (e.g., by administering the compound to a plant or animal host carrying or harboring undesired cells of interest, such as cancer cells, pathological microbial cells, parasitic cells, etc.)

Compounds of the present invention may also be used to control, e.g., kill or inhibit the growth of, microbes that may otherwise contaminate an industrial fermentation.

Additionally, compounds of the present invention may be used as an herbicide. The compounds of the present invention may be applied to the surface of the plant including, but not limited to, leaves, stems, flowers, fruits, roots, cells or callus tissue. Alternatively, the compounds of the present invention may be introduced into the plant via methods standard in the art including, but not limited to, microinjection, electroporation, particle bombardment, and *Agrobacterium*-mediated transformation.

Further, compounds of the present invention may also be used for treatment of infection of plants and plant cells by plant pathogens, the plant pathogens including, but not limited to, bacteria, fungi, oomycetes, viruses, and nematodes. For the purpose of treatment of plant pathogenic infections, the compounds of the present invention may be applied to the surface of a plant including, but not limited to, leaves, stems, flowers, fruits, roots, cells or callus tissue. Alternatively, the compounds of the present invention may be introduced into the plant via methods standard in the art including, but not limited to, microinjection, electroporation, particle bombardment, and *Agrobacterium*-mediated transformation.

The therapeutically effective dosage of any specific compound, the use of which is in the scope of present invention, will vary somewhat from compound to compound, and patient to patient, and will depend upon the condition of the patient and the route of delivery. As a general proposition, a dosage from about 0.1 to about 50 mg/kg will have therapeutic efficacy, with all weights being calculated based upon the weight of the active compound, including the cases where a salt is employed. In some embodiments, a dosage from about 10 mg/kg to about 50 mg/kg may be employed for oral administration. In some embodiments, a dosage from about 0.5 mg/kg to 5 mg/kg may be employed for intramuscular injection.

For agricultural use, the compounds may be applied to plants or crops by any suitable technique, such as by spraying.

The present invention is explained in greater detail in the following non-limiting Examples.

EXAMPLES

Developing DNA Aptamers to PSMA.

We have has formed an affinity matrix using recombinant PSMA expressed from baculovirus. This affinity matrix has been used in completion of two SELEX procedures to identify novel DNA aptamers to PSMA. These are the first DNA aptamers to PSMA that we are aware of. We contracted with Kinakeet Biotechnology (Richmond, Va.) to express the 706 amino acids comprising the extracellular domain of PSMA from Sf9 cells using baculovirus. RNA was extracted from pelleted LNCaP cells and primers were designed for cloning of the extracellular domain of PSMA from the corresponding cDNA. The accuracy of all cloning steps was verified by DNA sequencing. The recombinant protein was purified by affinity chromatography. Protein purity was determined by gel electrophoresis and the identity of the protein was confirmed by Western blotting and mass spectrometry. The recombinant PSMA includes a His-tag that was used for attachment of the recombinant protein to Dynabeads Talon (Dynal Biotech) for use as an affinity matrix for aptamer selection. The suitability of the affinity matrix for DNA aptamer selection was verified by demonstrating that the A10-3 RNA aptamer to PSMA bound the affinity matrix. SELEX methodology was used to identify DNA aptamers to PSMA. The DNA library used for SELEX included a 45 nucleotide random sequence flanked by two 21 nucleotide fixed regions. The ssDNA was converted to dsDNA using a series of "fill-in" reactions with T7 DNA polymerase. These "fill-in" reactions were each run on a 2 μg scale. The resulting dsDNA was amplified using multiplex PCR to create 20-30 μg of dsDNA. PCR was done using a primer to the original ssDNA that was 5'-phosphorylated. Following amplification, the dsDNA was converted to ssDNA using exonuclease λ. The ssDNA product was analyzed by gel electrophoresis and quantified by UV absorption. Typically 5-10 μg ssDNA were used for binding reactions for SELEX. The ssDNA was incubated with the PSMA affinity matrix for 60 min at 37° C. The supernatant was removed, and bound material was eluted from the affinity matrix by heating to 90° C. ssDNA was converted to dsDNA, PCR amplified, converted back to ssDNA and repeated rounds of forward and counter SELEX were performed to create a DNA pool enriched in sequences that bound with high affinity to PSMA. The resulting DNA was cloned into the pGEM T-Easy vector (Promega) which was then used to transform competent BL21 E. coli cells. DNA sequences were determined from individual clones at the core DNA sequencing facility of the CCCWFU. The initial SELEX procedure resulted in identification of 10 DNA sequences—several of which were chemically synthesized and shown to bind selectively to recombinant PSMA (BSA as the negative control) using fluorescence anisotropy. These sequences were also shown using fluorescence microscopy to bind selectively to PSMA-expressing prostate cancer cells (LNCaP, C4-2) relative to PC3 cells. While we had identified DNA aptamers that were suitable for the next stage of Cytotoxamer development, a few of our experiments using scrambled sequences as negative controls had ambiguous results. Further, while we consistently observed surface binding to PSMA-expressing cells by fluorescence microscopy, we observed little evidence for cellular internalization. Somewhat surprisingly, only surface binding was also observed with the A10 RNA aptamer that was reported to be internalized into PSMA-expressing cells by other research groups (Lupold et al., 2002; Chu et al., 2006). We thus decided to repeat the SELEX procedure. The second SELEX procedure used different primer sequences, but was otherwise undertaken using identical methodology. Sequencing of 10 clones from this procedure resulted in nine of the clones having a single sequence indicating the final DNA pool was highly enriched in this sequence which we termed PSMA01. The sequence of PSMA01 is:

```
5'-GCGTTTTCGCTTTTGCGTTTTGGGTCATCTGCTTACGATAGCAATCGT    (SEQ ID NO: 1)
```

Studies with the PSMA01 DNA aptamer verified that this sequence selectively binds to PSMA-expressing cells and has no affinity for cells that do not express PSMA (FIG. 1). In these studies, live (non-fixed cells) cells were incubated in the presence of fluorescently-labeled aptamer for 2 h at room temperature. In these studies, C4-2 and LNCaP cells were used to evaluate binding to PSMA+ cells while PC3 cells were used as a PSMA– negative control. The PSMA01 DNA aptamer that we identified in our laboratory displayed selective binding to PSMA+C4-2 and LNCaP cells and displayed no binding to PSMA–PC3 cells. The binding of PSMA-01 was similar to the A10-3 RNA aptamer that had been previously described. Neither our PSMA-01 DNA aptamer nor the A10-3 aptamer were internalized into PSMA+ cells to any significant extent under any of the conditions analyzed (incubation at room temperature or 37° C.).

Figure 3:
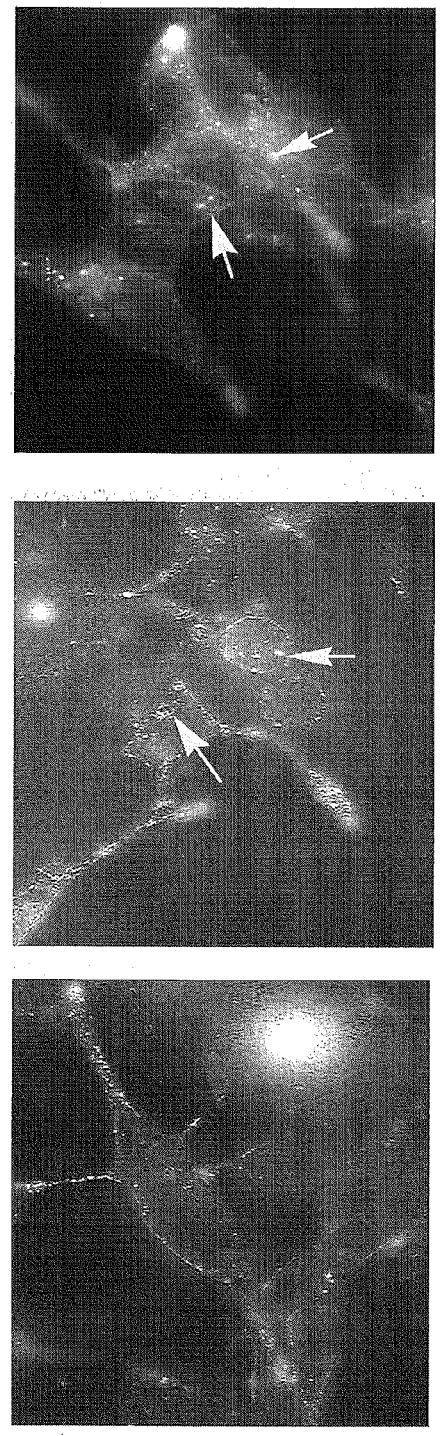
FIG. 3. Fluorescence microscopy images of (A) a monomeric aptamer conjugate of PSMA01 with a dT16 tail; (B) a dimeric aptamer complex consisting of 1:1 ratio of monomeric PSMA01 conjugates with dA16 and dT16 tails; (C) the J591 mAb. All images were obtained using live C4-2 cells. For (A) and (B) cells were prepared as described in FIG. 4. For (C), live cells were incubated with J591, fixed with formalin, permeabilized with 0.5% Triton-X prior to addition of secondary antibody (goat anti-mouse) and post-fixed with formalin prior to visualization. Yellow arrows point to internalized signal.
Figure 2:
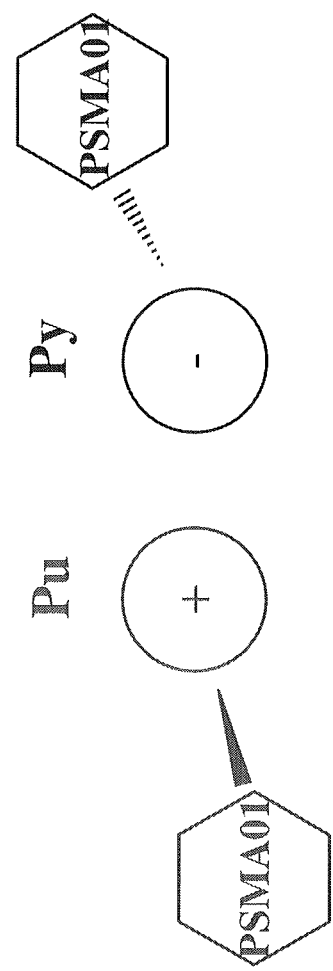
FIG. 2. Depiction of dimeric aptamer complex formation through Watson-Crick base pair formation. PSMA01 aptamers were synthesized with either a dA16 (SEQ ID NO: 2) or dT16 (SEQ ID NO: 3) tail and dimers were formed upon annealing the individual aptamer conjugates in a 1:1 ratio.
Figure 2:
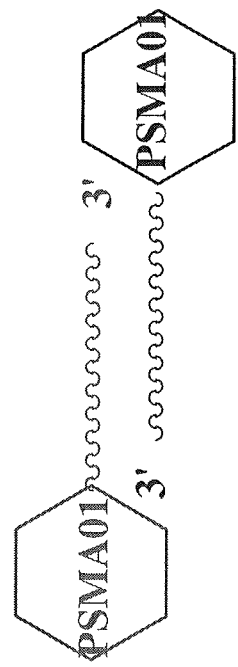

Dimeric Aptamer Complexes Show Enhanced Cellular Internalization: At this time, we obtained a sample of the J591 mAb to PSMA (kindly provided by Dr. Neil Bander, Cornell-Weill Medical School). During the course of studies with J591, it became clear that the mAb not only had somewhat greater surface binding to PSMA-expressing cells relative to PSMA01 (and other aptamers, both DNA aptamers developed in our laboratory and RNA aptamers that had been previously described), but J591 was also more efficiently internalized into PSMA-expressing cells. In contemplating the physical basis for the increased binding and internalization of the J591 antibody relative to the monomeric aptamer conjugates, we focused on the bivalent structure of the mAb as likely contributing significantly to the observed more favorable binding and cellular internalization characteristics of the mAb. We designed bivalent dimeric aptamer complexes that were formed through Watson-Crick base pairing (FIG. 2). Initial constructs used homopolymeric dA and dT tails since this strategy readily permits rendering these dimeric aptamer complexes potentially cytotoxic through T→FdU substitution. The tails were designed to form a 16 base pair linker sequence that would be stable at 37° C. but not be so stable as to inhibit nuclease degradation following cellular internalization. Although this linker is probably not of optimal geometry, the dimeric aptamer complex displayed greater surface binding and fluorescence microscopy images were consistent with increased cellular internalization relative to the monomeric aptamer conjugates (FIG. 3).

Figure 4:
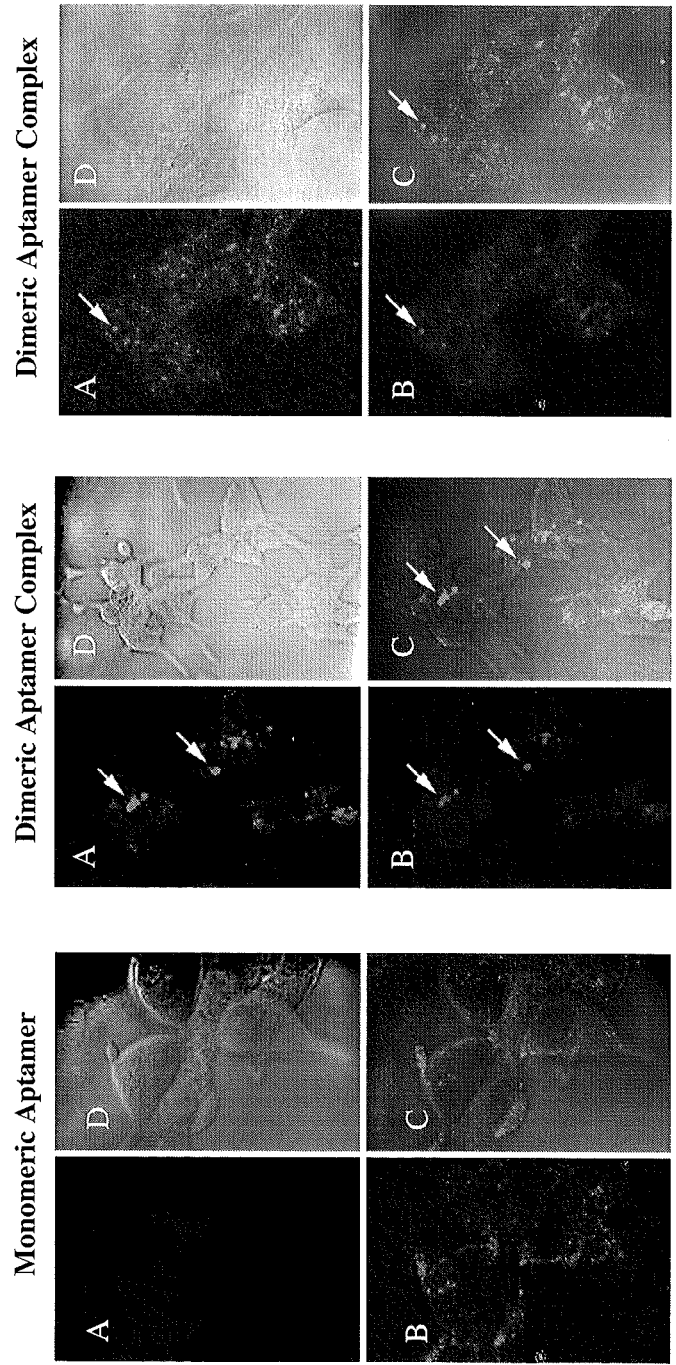
FIG. 4. Split x-y images using confocal microscopy to detect two fluorescent dyes (Quasar 670 and Quasar 570). The PSMA01 aptamer with the dA16 tail was labeled with Quasar 670 while the PSMA01 aptamer with the dT16 tail was labeled with Quasar 570. The unconjugated PSMA01 aptamer was also labeled with Quasar 570. In each panel of four images is shown: (A) Quasar 670 image; (B) Quasar 570 image; (C) overlay of (A) and (B); (D) Nomarski image. (Left) The PSMA01 monomeric aptamer is shown in the leftmost panel; (Center) Dimeric aptamer complex consisting of a 1:1 stoichiometry of PSMA01 aptamers with dA16 and dT16 tails; (Right) Dimeric Aptamer Complexes that also contain a flexible linker (see FIG. 5). The dimeric aptamer complex has greater internalized signal relative to the monomeric aptamer. Inclusion of the alkyl spacer results in enhanced cellular internalization relative to dimeric complexes that do not have alkyl spacer (see FIG. 9). Arrows point to internalized aptamer.

Confocal Microcopy Demonstrates Enhanced Cell Internalization of Dimeric Aptamer Complexes:

The cellular internalization of dimeric aptamer complexes was further investigated using confocal microscopy. For these studies, both component monomeric aptamer conjugates were fluorescently labeled. PSMA01-dA16 was labeled with Quasar 670 and PSMA01-dT16 was labeled with Quasar 570. These long wavelength dyes are resistant to bleaching and have minimal spectral overlap permitting simultaneous scanning of these two wavelengths to demonstrate through co-localization studies to what extent the dimer structure was formed and whether the aptamer remained in dimeric form while bound to the cell surface and following cellular internalization. Representative images are shown in FIG. 4. The data confirmed co-localization of the Quasar 570 and Quasar 670 dyes indicating that the aptamer complexes bound as dimers. The images indicated cellular internalization and retention of the dimeric complexes within endocytic vesicles. The two dyes co-localized in endocytic vesicles, as well, consistent with the aptamer complex remaining in dimeric form following cellular internalization.

Figure 5:
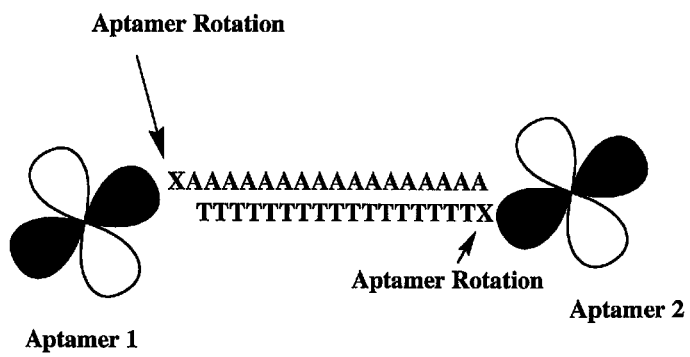
FIG. 5. Inclusion of flexible alkyl spacers (denoted by "X") in dimeric aptamer complexes with either a dA17 (SEQ ID NO: 4) or dT17 (SEQ ID NO: 5) tail. The flexible linkers allow each aptamer to rotate relative to the linker construct to obtain maximal binding affinity.

Increased Flexibility Enhances Cellular Uptake of Dimeric Aptamer Complexes:

While the linker domain consisting of 16 Watson-Crick base pairs was stable at 37° C. and conferred an advantage in terms of cellular binding and internalization relative to the monomeric aptamer conjugates, we reasoned that additional binding avidity of the dimeric aptamer complex for PSMA could be conferred by including one or more alkyl linkers into the structure. Alkyl linkers are highly flexible, with flexibility that surpasses the deoxyribonucleotide components of the dsDNA that composes the linker sequence (FIG. 5). We reasoned that this increased flexibility would allow each component aptamer to adopt an optimal conformation for binding to PSMA with minimal penalty in terms of free energy associated with structural distortion. Preliminary studies are promising, with dimeric aptamer complexes including one alkyl linker between the PSMA01 aptamer and the tail (either dA16 or dT16) showing enhanced cellular binding and internalization relative to dimeric aptamer complexes that do not include an alkyl linker (FIG. 4).

Figure 6:
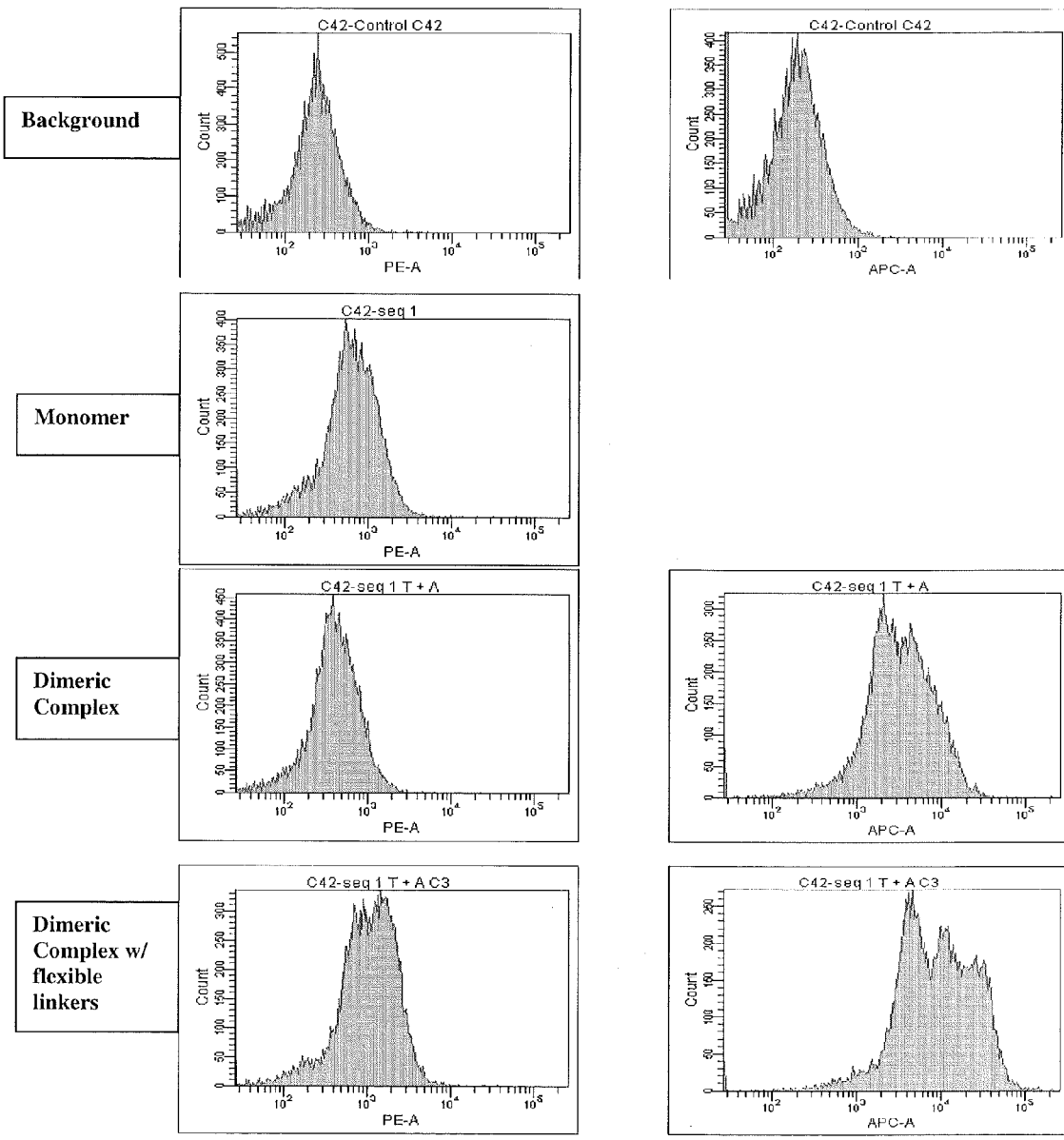
FIG. 6. Flow cytometry evaluation of the binding of fluorescently labeled aptamers and dimeric aptamer complexes with and without flexible linkers to C4-2 cells. Aptamer labeling with Quasar 570 and Quasar 670 was done as described in FIG. 8. The mean fluorescence intensity for the monomeric aptamer is right-shifted relative to background. Monitoring of Quasar 670 fluorescence clearly shows the dimeric complex shifted relative to background. Introduction of flexible linkers further increases the mean fluorescence intensity. The results are consistent with dimeric aptamer complexes having enhanced cellular binding relative to monomeric aptamers and with flexible linkers further enhancing cell binding.

The relative binding of the PSMA01 DNA aptamer in monomeric form as well as in dimeric form with and without flexible linkers was also evaluated towards C4-2 cells using flow cytometry. The results are summarized in FIG. 6. Cells were treated in the same manner as described for the confocal microscopy experiments and were detached using an enzyme-free cell-dissociation buffer (Invitrogen). Cells were analyzed using a BD FACSCanto flow cytometry system and the data were analyzed using BD FACSDiva software (BD Biosciences, San Jose, Calif.).

Figure 7:
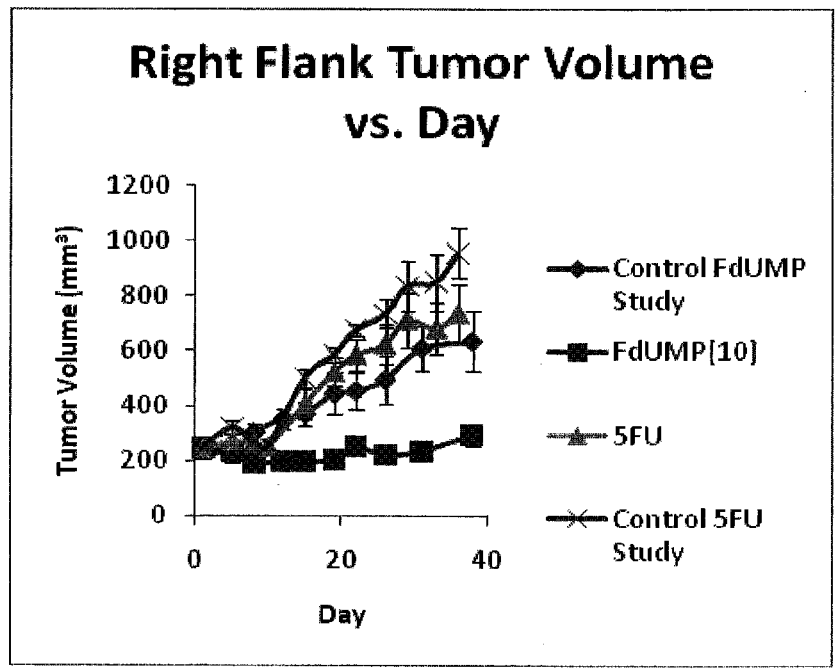
FIG. 7. Plot of tumor size versus time for PC3 xenografts in nude mice. Data are shown for four treatment groups (n=8 in each group): 1) control 1; 2) FdUMP[10]; 3) control 2; 4) 5-FU. The FdUMP[10] and 5FU studies were done consecutively (rather than concurrently) so that two control groups were required. Tumors from animals treated with FdUMP [10] displayed statistically significant reduced growth throughout the study while 5FU did not reduce tumor growth rates relative to control.

Safety and Efficacy of FdUMP[10] Towards Prostate Cancer Xenografts:

The principal strategy that will be used to render the dimeric aptamer complexes we have developed selectively cytotoxic towards targeted cancer cells is to include cytotoxic nucleotides, such as FdU, in the structure. While other modalities may also be included to render these modified aptamers cytotoxic to cancer cells (e.g. siRNA, toxins), there is considerable merit to the concept that dimeric aptamer complexes are the best method for delivery of FdU and other cytotoxic nucleotide analogs in the future. In principle, delivery of cytotoxic nucleotide analogs in aptamers increases the selectivity and potency of these drugs while minimizing systemic toxicities. In this regard, it is important to consider the advantages obtained by inclusion of FdU in single-stranded DNA (e.g. FdUMP[10]) relative to delivery as the nucleobase (5FU). We have shown that not only does delivery of fluoropyrimidine (FP) as FdUMP[10] increase efficacy and decrease toxicity, it also changes the spectrum of malignancies that are responsive to FP treatment. Recent unpublished data from our laboratory has demonstrated that FdUMP[10] is efficacious towards PC3 xenografts, a model of hormone-refractory prostate cancer (FIG. 7). PSMA, the target for the dimeric aptamer complexes being developed by us, is frequently expressed in advanced prostate cancer. PSMA is also frequently expressed in tumor neovasculature. As FPs are widely used for treatment of solid tumors, the dimeric aptamer complexes developed in these studies should provide an improved mechanism for tumor-specific delivery of FPs.

Figure 8:
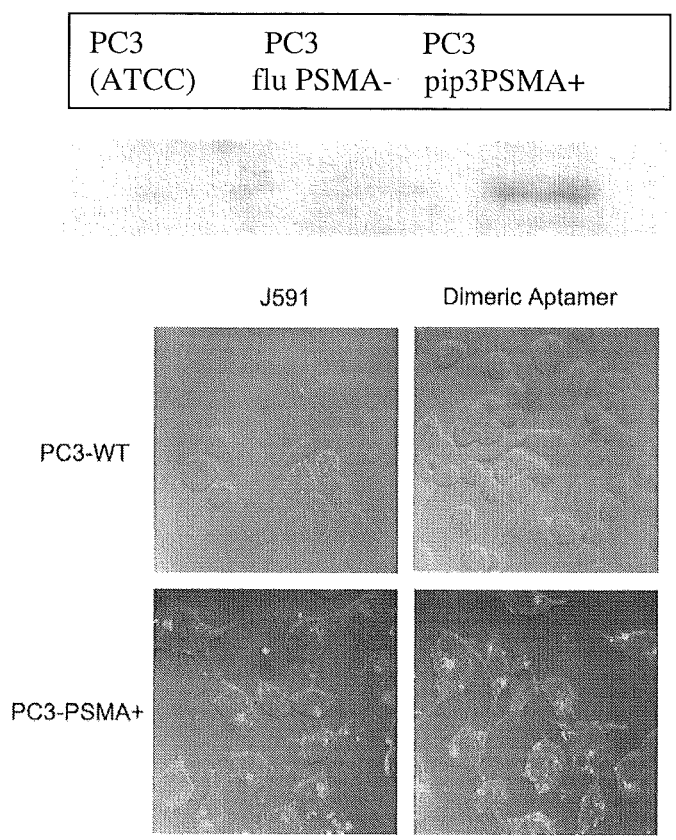
FIG. 8. (Top) Western blot demonstrating expression of PSMA in PSMA-transduced PC3 cells but not in mock-transfected PC3 cells or PC3 cells obtained from ATCC. (Bottom)—Confocal microscopy images demonstrating a lack of binding by both the J591 mAb and the dimeric aptamer complex to PSMA−PC3 cells (top panels). Significant surface binding is observed for both the dimeric aptamer complex and the mAb to the PSMA+PC3 cells (bottom panels).

We recently completed an in vivo xenograft study evaluating the anti-tumor activity of FdUMP[10] and 5FU towards PC3 xenografts (FIG. 8). All groups had comparable size tumors at baseline. FdUMP[10] (150 mg/kg) was injected i.v. 1× per week via jugular vein catheter. 5FU (100 mg/kg) was also injected 1× per week by the same route. The dose of 5FU administered was the maximum tolerated dose and 5FU-treated animals lost weight compared to the controls. FdUMP[10] was well-tolerated at the administered dose. A mixed effects model was fit to examine whether there were differences between groups over the first 44 days after administration of FdUMP[10] or 5FU. In this model, individual animals were considered as random effects and the group and day variables were considered as fixed effects. The FdUMP[10]-treated mice displayed significantly reduced tumor growth relative to control beginning on day 18 of treatment and persisting for all subsequent time points ($p<0.0003$ (day 30)). We expect that with dimeric aptamer complexes including FdU, we will further increase the selectivity for malignant cells and further reduce systemic toxicities. Thus, dimeric aptamer complexes may ultimately become the preferred method for administering fluoropyrimidine chemotherapy in the era of molecularly targeted cancer therapeutics.

We plan to conduct clonogenic assays with dimeric aptamer complexes containing FdU in a matched pair of PC3 cells (PSMA+ and PSMA−). These cells were provided by Dr. W. D. Heston (Cleveland Clinic). Since these cells differ only in PSMA expression, differences in cytotoxicity can be attributed directly to PSMA-mediated endocytosis of dimeric aptamer complexes. PC3 cells also have mutant p53 while C4-2 cells have wtp53. Ongoing studies from our laboratory show that PC3 cells are more sensitive to activated FPs (e.g. FdUMP[10] than C4-2 cells and that the relative cytotoxicity difference can be reduced either by shRNA knockdown of p53 in C4-2 cells or viral transduction of wtp53 into PC3 cells. As p53 mutations are among the most frequent mutation in cancer and that mutated p53 generally makes tumors less responsive to chemotherapy, these finding bode well for the future clinical use of activated FPs, and especially dimeric aptamer complexes containing FdU, for molecularly-targeted chemotherapy.

Selective Uptake into PC3 PSMA+/− Cells.

We have evaluated the selective binding and uptake of our dimeric aptamer complexes using in a matched pair of PC3 cells (PSMA+ and PSMA−). These cells were provided by Dr. W. D. Heston (Cleveland Clinic). Since these cells differ only in PSMA expression, differences in surface binding and internalization can be attributed directly to PSMA-mediated processes. Western blots confirmed PSMA expression selectively in the PSMA-transduced PC3 cells (FIG. 8). Representative confocal images demonstrating PSMA-specific binding are also shown in FIG. 8. Neither the J591 mAb nor the dimeric aptamer complex displayed either surface binding or internalization into the PSMA−PC3 cells. Both the mAb and the dimeric aptamer complex, however, displayed considerable surface binding upon incubation with the PSMA+ PC3 cells at 4° C. and considerable internalized signal was evident upon incubation at 37° C. When incubation proceeds at 4° C., clustered signal, or surface "patching" is observed for both the J591 mAb and the dimeric aptamer complex. This surface "patching" (Hopwood et al., 1982) is observed over the Golgi apparatus in PSMA+ PC3 cells. Patching is characteristic of multivalent ligands and facilitates endocytosis. Both the dimeric aptamer complex and the mAb are present in internalized vesicles in PSMA+ PC3 cells following incubation at 37° C.

The foregoing is illustrative of the present invention, and is not to be construed as limiting thereof. The invention is defined by the following claims, with equivalents of the claims to be included therein.

That which is claimed is:

1. A method of introducing a nucleic acid of interest into a cell of interest, comprising contacting a composition to said cell under conditions in which said nucleic acid of interest is internalized into said cell;

said composition comprising a pair of compounds, at least one member of said pair of compounds comprising said nucleic acid of interest, and each member of said pair having a second nucleic acid that is complementary to and hybridized to the second nucleic acid of the other member of said pair;

each of said compounds independently having the formula A-B-C, wherein:

A is a first nucleic acid that specifically binds to an extracellular surface protein expressed by a cell of interest, B is an alkyl linker; and C is said second nucleic acid;

wherein said first and/or second nucleic acid of at least one of said compounds comprises poly-FdUMP; and wherein said second nucleic acid of each of said compounds is DNA.

2. The method of claim 1, wherein at least one of said first nucleic acids is an aptamer.

3. The method of claim 1, wherein at least one of said first nucleic acids is from 30 to 150 nucleotides in length.

4. The method of claim 1, wherein at least one of said first nucleic acids is selected from the group consisting of DNA and RNA.

5. The method of claim 1, wherein at least one of said alkyl linkers comprises C2-C6 loweralkyl.

6. The method of claim 1, wherein at least one of said second nucleic acids is from 8 to 100 nucleotides in length.

7. The method of claim 1, wherein said cell of interest is a cancer cell.

8. The method of claim 1, wherein at least one of said extracellular surface proteins is an extracellular surface protein differentially expressed by cancer cells.

9. The method of claim 8, wherein at least one of said extracellular surface proteins comprises an extracellular surface portion of prostate specific membrane antigen (PSMA).

10. The method of claim 1, wherein said composition is in a pharmaceutically acceptable carrier.

11. The method of claim 1, wherein said method is carried out in vitro.

12. The method of claim 1, wherein:

at least one of said first nucleic acids is DNA.

13. The method of claim 1, wherein said poly-FdUMP is selected from the group consisting of FdUMP[5] and FdUMP [10].

14. The method of claim 1, wherein one of said second nucleic acids comprises a poly-A from 10 to 40 nucleotides in length and the other of said second nucleic acids comprises a poly-T from 10 to 40 nucleotides in length, and wherein said poly-A and said poly-T are hybridized to each other.

15. A method of introducing a nucleic acid of interest into a cell of interest, comprising contacting a composition to said cell under conditions in which said nucleic acid of interest is internalized into said cell;

said composition comprising a pair of compounds, at least one member of said pair of compounds comprising said nucleic acid of interest, and each member of said pair having a second nucleic acid that is complementary to and hybridized to the second nucleic acid of the other member of said pair;

each of said compounds independently having the formula A-B-C, wherein:

A is a first nucleic acid that specifically binds to an extracellular surface protein expressed by a cell of interest, B is an alkyl linker; and C is said second nucleic acid;

wherein said first and/or second nucleic acid of at least one of said compounds comprises poly-FdUMP, and wherein each of said compounds further comprises a flexible alkyl linker included within said second nucleic acid.

16. The method of claim 15, wherein said alkyl linker and said flexible alkyl linker of at least one of said compounds comprises C2-C6 loweralkyl.

17. The method of claim 15, wherein said poly-FdUMP is selected from the group consisting of FdUMP[5] and FdUMP [10].

18. The method of claim 15, wherein at least one of said second nucleic acids is from 10 to 40 nucleotides in length.

19. The method of claim 15, wherein at least one of said compounds further comprises doxorubicin.

20. A method of introducing a nucleic acid of interest into a cell of interest, comprising contacting a composition to said cell under conditions in which said nucleic acid of interest is internalized into said cell;

said composition comprising a pair of compounds, at least one member of said pair of compounds comprising said nucleic acid of interest, and each member of said pair having a second nucleic acid that is complementary to and hybridized to the second nucleic acid of the other member of said pair;

each of said compounds independently having the formula A-B-C, wherein:

A is a first nucleic acid that specifically binds to an extracellular surface protein expressed by a cell of interest, B is an alkyl linker; and C is said second nucleic acid;

wherein said first and/or second nucleic acid of at least one of said compounds comprises a cytotoxic nucleoside or nucleotide; and wherein said second nucleic acid of each of said compounds is DNA.

21. The method of claim 20, wherein said extracellular surface protein expressed by the cell of interest forms dimers.

22. The method of claim 21, wherein said extracellular surface protein is selected from PSMA and transferrin receptor.

23. The method of claim 20, wherein one of said second nucleic acids comprises a poly-A from 10 to 40 nucleotides in length and the other of said second nucleic acids comprises a poly-T from 10 to 40 nucleotides in length, and wherein said poly-A and said poly-T are hybridized to each other.

24. The method of claim 20, wherein each of said compounds further comprises a flexible alkyl linker included within said second nucleic acid.

25. A method of introducing a nucleic acid of interest into a cell of interest, comprising contacting a composition to said cell under conditions in which said nucleic acid of interest is internalized into said cell;

said composition comprising a pair of compounds, at least one member of said pair of compounds comprising said nucleic acid of interest, and each member of said pair having a second nucleic acid that is complementary to and hybridized to the second nucleic acid of the other member of said pair;

each of said compounds independently having the formula A-B-C, wherein:
A is a first nucleic acid that specifically binds to an extracellular surface protein expressed by a cell of interest,
B is an alkyl linker; and
C is said second nucleic acid;
and wherein at least one of said first nucleic acids is a DNA having the sequence of SEQ ID NO: 1.

* * * * *

```
                            SEQUENCE LISTING

<160> NUMBER OF SEQ ID NOS: 5

<210> SEQ ID NO 1
<211> LENGTH: 48
<212> TYPE: DNA
<213> ORGANISM: Artificial
<220> FEATURE:
<223> OTHER INFORMATION: PSMA01 DNA aptamer sequence

<400> SEQUENCE: 1
gcgttttcgc ttttgcgttt tgggtcatct gcttacgata gcaatcgt                 48

<210> SEQ ID NO 2
<211> LENGTH: 16
<212> TYPE: DNA
<213> ORGANISM: Artificial
<220> FEATURE:
<223> OTHER INFORMATION: dA16 tail of PSMA01 aptamer

<400> SEQUENCE: 2
aaaaaaaaaa aaaaaa                                                    16

<210> SEQ ID NO 3
<211> LENGTH: 16
<212> TYPE: DNA
<213> ORGANISM: Artificial
<220> FEATURE:
<223> OTHER INFORMATION: dT16 tail of PSMA01 aptamer

<400> SEQUENCE: 3
tttttttttt tttttt                                                    16

<210> SEQ ID NO 4
<211> LENGTH: 17
<212> TYPE: DNA
<213> ORGANISM: Artificial
<220> FEATURE:
<223> OTHER INFORMATION: Poly dA tail connected to alkyl linker of
      PSMA01 DNA aptamer
<220> FEATURE:
<221> NAME/KEY: misc_feature
<222> LOCATION: (1)..(1)
<223> OTHER INFORMATION: Alkyl linker connected to 5' A

<400> SEQUENCE: 4
aaaaaaaaaa aaaaaaa                                                   17

<210> SEQ ID NO 5
<211> LENGTH: 17
<212> TYPE: DNA
<213> ORGANISM: Artificial
<220> FEATURE:
<223> OTHER INFORMATION: Poly dT tail connected to alkyl linker of
      PSMA01 DNA aptamer
<220> FEATURE:
<221> NAME/KEY: misc_feature
<222> LOCATION: (1)..(1)
<223> OTHER INFORMATION: Alkyl linker connected to 5' T

<400> SEQUENCE: 5
tttttttttt ttttttt                                                   17
```